United States Patent [19]

Trueman

[11] Patent Number: 5,413,554
[45] Date of Patent: May 9, 1995

[54] HAND SPLINT AND EXERCISER

[76] Inventor: Constance C. Trueman, 585 Indian Road, Mississauga, Ontario, Canada, L5H 1R1

[21] Appl. No.: 210,839

[22] Filed: Mar. 4, 1994

[51] Int. Cl.$^6$ .......................... A61F 5/00; A63B 23/16
[52] U.S. Cl. ........................ 602/21; 482/48; 601/40
[58] Field of Search .................... 602/20–22; 128/877–880; 482/44, 47, 48; 601/23, 33, 40; 2/16

[56] References Cited

U.S. PATENT DOCUMENTS

| | | |
|---|---|---|
| 4,602,620 | 7/1986 | Marx .................. 602/21 |
| 4,644,938 | 2/1987 | Yates et al. .............. 601/40 |
| 4,765,320 | 8/1988 | Lindemann et al. ............ 602/22 |
| 4,809,688 | 3/1989 | Aymerica del Valle et al. ... 602/21 |
| 4,949,711 | 8/1990 | Gyovai et al. ............ 602/21 |

OTHER PUBLICATIONS

Rehabilitation of the Hand-Surgery & Therapy, Published by C. V. Mosby Co. 1990 pp. 390 to 409.
Rehabilitation of the Hand-Surgery & Therapy, Published by C. V. Mosby Co. 1990 pp. 427 to 557.
Journal of Hand Therapy-Published by Hanley & Belfus, Inc. Apr. 1990 Advertisement by BIOMET Inc.
Journal of Hand Therapy-Published by Hanley & Belfus, Inc. Apr. 1989 pp. 71 to 83.
Journal of Hand Therapy-Published by Hanley & Belfus, Inc. Apr. 1989 pp. 102 to 106.

*Primary Examiner*—Linda C. M. Dvorak
*Attorney, Agent, or Firm*—Rogers & Scott

[57] ABSTRACT

The invention provides a device made up of a combination of a splint for dorsal protection and an exerciser in which the exerciser applies a force which mimics the natural forces applied by the tendons of the finger. The finger then moves and bends at all three finger joints in a more natural manner with minimal application of tensile forces to the finger and without significant loading on the root of the finger.

7 Claims, 3 Drawing Sheets

5,413,554

HAND SPLINT AND EXERCISER

BACKGROUND OF THE INVENTION

This invention relates to a device for use in therapy of the hand and more specifically to a device for exercising a finger after surgery on the finger. The device is particularly useful after surgical reattachment or graft of a severed tendon.

Injuries to hands often result in damage to fingers, particularly on the parts of the finger used to grip, (the inside of the finger). These parts can be torn or cut by contact with sharp items when they are gripped by the hand. Other injuries are caused by impacts and it is not uncommon for corrective surgery to be needed to reattach or graft tendons, restore stiff joints, or for similar reasons. After such surgery, it is essential that the finger be kept mobile to minimize adverse scar adhesions which can result in immobilization of the finger if allowed to heal without movement. It is therefore common practice to provide some kind of splint to support and protect the injured hand and at the same time provide some kind of device which will permit controlled manipulation of the finger by the patient within a desired range of movements.

A common practice is to use a splint to give dorsal protection and to attach a lanyard to the tip of the finger in question so that pulling on the lanyard will bend the finger toward the palm of the hand. Unfortunately as the finger bends, the force causes a tensile loading in the tip of the finger which tends to cause bending only at the root of the finger rather than in the joints of the finger where the movement is required. Although such an approach is better than leaving the finger immobile, it must be used carefully to avoid damage to the repair. Because of the accompanying pain the patient may not use the device, and consequently adverse scar adhesions form which, as mentioned, can have most undesirable results.

SUMMARY OF THE INVENTION

One of the objects of the present invention is to provide a device which overcomes the disadvantages of the prior devices. Accordingly, the invention provides a device made up of a combination of a splint for dorsal protection and an exerciser in which the exerciser applies a force which mimics the natural forces applied by the tendons of the finger. The finger then moves and bends at all three finger joints in a more natural manner with minimal application of tensile forces to the tip of the finger and without significant loading on the root of the finger.

BRIEF DESCRIPTION OF THE DRAWINGS

The invention will be better understood with reference to the drawings, in which.

DETAILED DESCRIPTION OF THE PREFERRED EMBODIMENT

Figure 1:
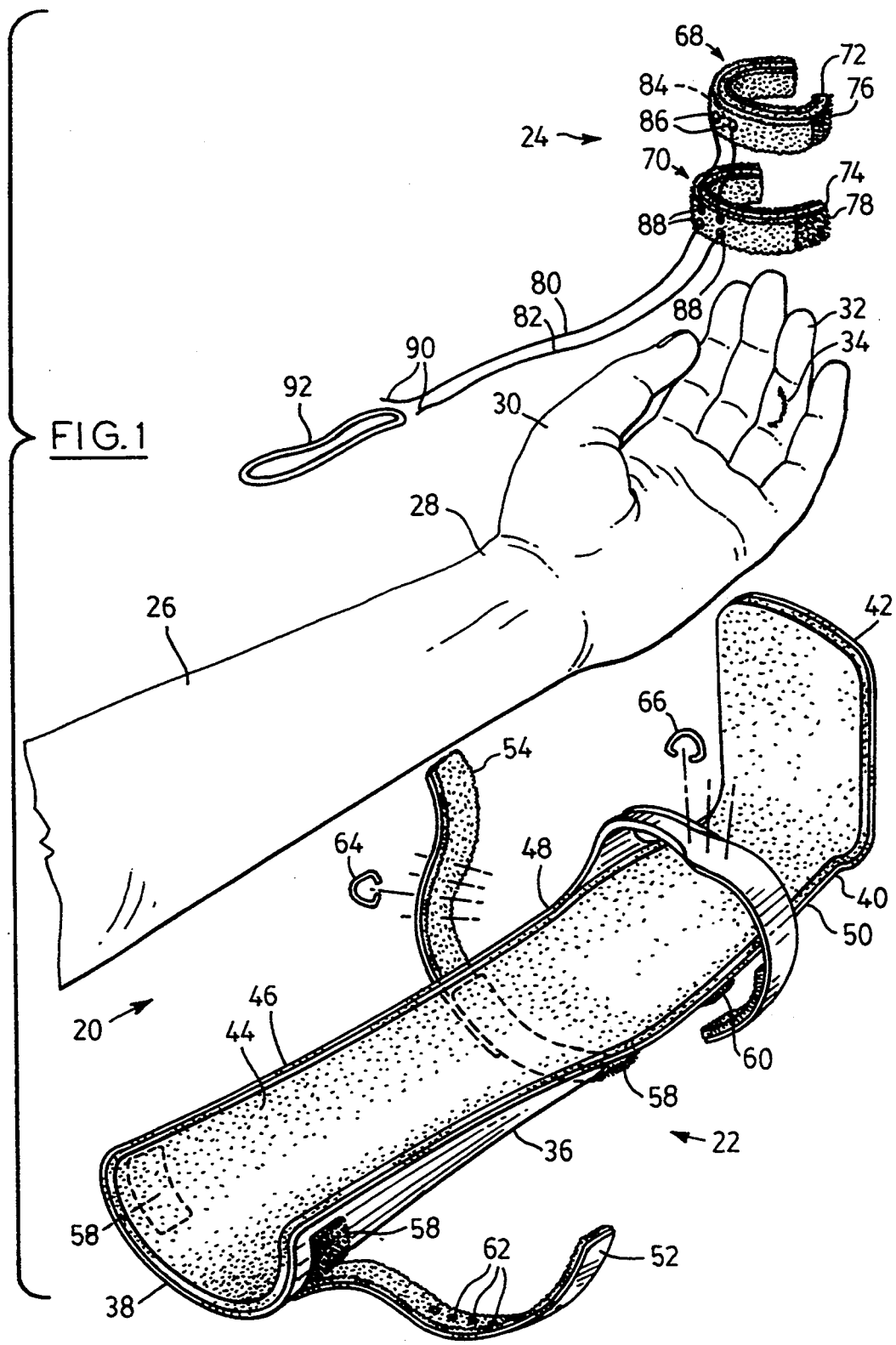
FIG. 1 is an exploded isometric view of a device for therapy of the hand according to a preferred embodiment of the invention and showing the parts of the device about to be assembled on a user's forearm, wrist and hand.

Reference is made firstly to FIG. 1 to describe parts of a device indicated generally by the numeral 20 and consisting essentially of two parts, namely a splint 22 and an exerciser 24 which combine to form the device. A user's forearm 26, wrist 28 and hand 30 are also shown in FIG. 1 for the purposes of relating the invention to a user. The hand 30 includes a third finger 32 which is to be treated to assist in returning the finger to normal use after a corrective operation on the finger indicated diagrammatically by a scar 34. It should be emphasized that the device is intended for use almost immediately after surgery and the scar 34 is intended to indicate the visible result of that surgery.

Figure 2:
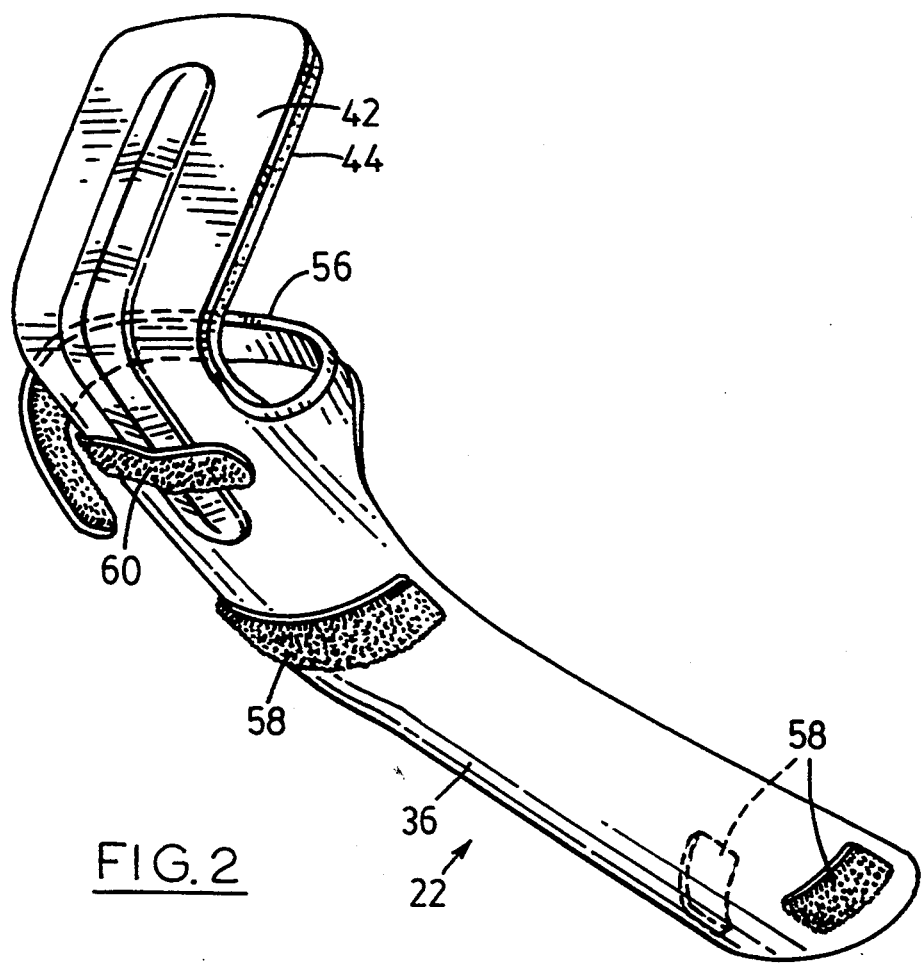
FIG. 2 is an isometric view drawn essentially from the right and bottom of FIG. 1 and illustrating a splint forming part of the device.

The splint 22 consists of a support 36 extending from a proximal end 38 to a distal end 40 where it meets a finger stop 42 angled upwardly as drawn with respect to the support 36. The splint is preferably formed using known techniques from a thermoplastic material sold for the purpose and which includes a soft lining 44 inside the splint where it will be in contact with the arm to further enhance the comfort of using the splint by cushioning the fingers during exercise. The material can be deformed about the user's forearm 26, wrist 28, and the main part of the hand 30 to better immobilize and control these parts of the arm. Consequently, the splint main support 36 has corresponding forearm, wrist and hand portions 46, 48, and 50. Associated with these parts are arm, wrist and hand straps 52, 54 and 56. The strap 56 is made integrally from the material of the splint but may be made as a separate piece and attached, whereas the straps 52 and 54 are attached at both ends using Velcro (registered trademark) patches 58 seen in FIG. 2. As also seen in FIG. 2, a further Velcro patch 60 is provided for receiving a hand strap 56. It will be appreciated that straps are provided with suitable material to combine with the respective Velcro patches as is common in the art to make attachments to retain straps in position.

Returning to FIG. 1, the forearm strap 52 is provided with an opening 62 for purposes which will be described. The wrist strap 54 receives a metal loop 64 and a similar loop 66 is provided on the hand strap 56. These are positioned under the fabric of the straps and attached permanently. The purpose of these parts will become evident with reference to FIGS. 2 and 3.

Returning now to the exerciser 24 also shown in FIG. 1, respective distal and proximal finger attachments 68, 70 consist of respective soft straps 72, 74 which are preferably permeable to minimize perspiration build up and which have Velcro attachments 76, 78 at the ends for engagement with suitable material on the inside of the straps so that these attachments can be wrapped around the finger and they can be adjusted and held in place simply by overlapping the ends of the straps. A pair of lanyards 80, 82 are made from a continuous piece of nylon monofilament of the type used in fishing line. They meet at a bight 84 and pass through a pair of openings 86 in the distal attachment 68 and through two pairs of openings 88 in the proximal attachment 70 such that the lanyards are free to ride through these openings 88 for purposes which will be described. The lanyards continue to free ends 90 and the exerciser is completed by an elastomeric loop or band 92.

Figure 3:
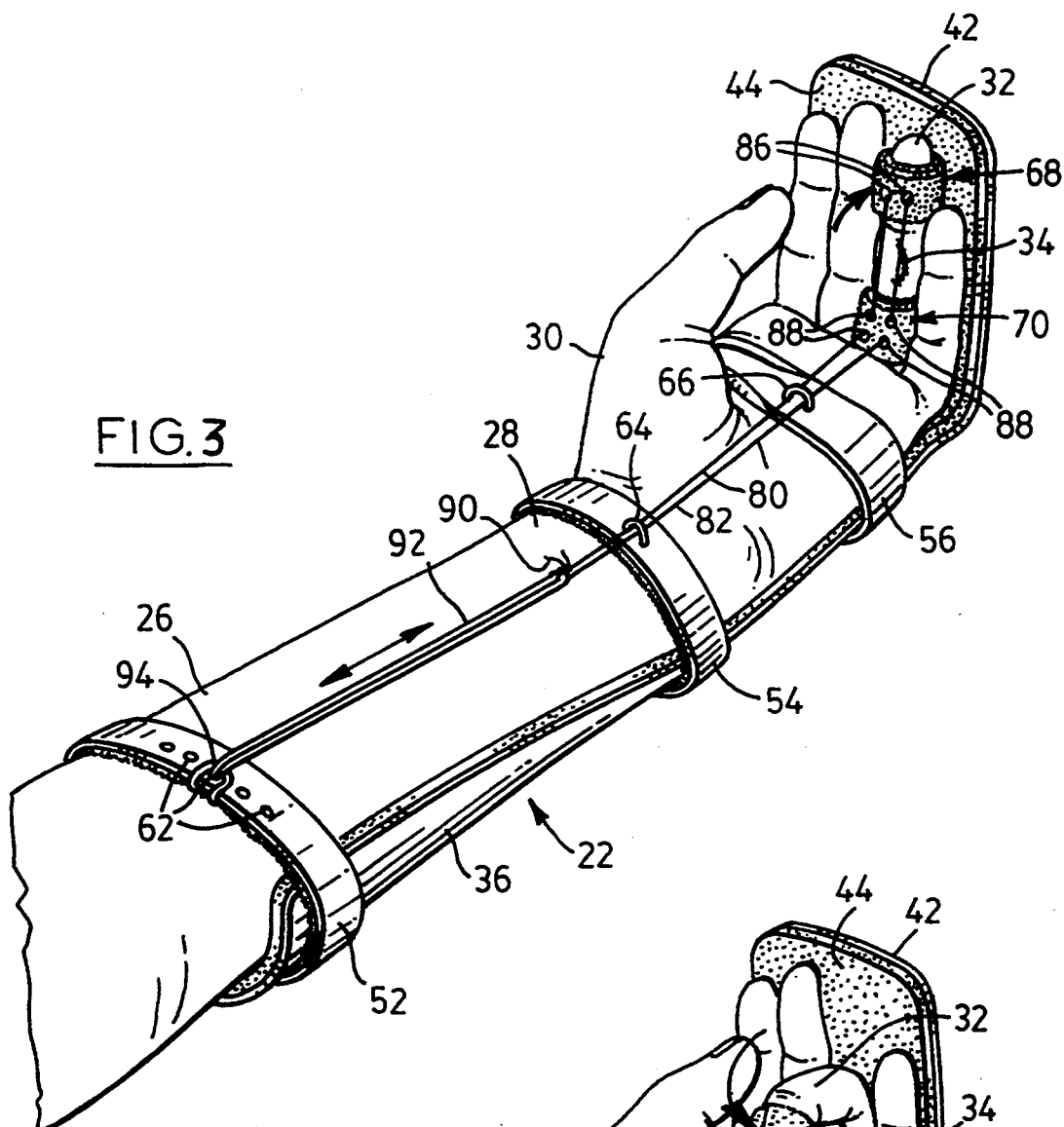
FIG. 3 is a view similar to FIG. 1 and showing the device after assembly on a user's arm and hand.

Reference is next made to FIG. 3 which illustrates the assembly of the parts described with reference to FIG. 1. As seen in FIG. 3, the user's arm and hand are now positioned and held in the splint 22 by the respective straps 52, 54, 56. The hand is positioned so that the fingers are resting comfortably against the stop 42 with the base joints bent and the fingers bent by the device. As a result the fingers can be straightened but the hand can not be accidently extended into a flat condition. This restricted movement is necessary to protect against damage to the wound resulting from the surgery in the third finger 32. This finger has received the respective distal and proximal attachments 68, 70 with the attachment 68 adjacent the tip or distal end of the finger and the attachment 70 at the root of the finger immediately adjacent the main portion or palm of the hand and around the proximal bone. As seen in the exemplary drawings, the wound is clear of the attachments 68, 70. However these attachments are readily adjusted for use over repairs and can be wrapped over dressings and adjusted as the need arises.

The exerciser 24 is now positioned with the lanyards 80, 82 tensioned slightly by virtue of attachment of the ends 90 to the elastomeric loop 92. This loop is engaged through one of the openings 62 in the strap 52 and then passed through itself to form an anchor 94 at the strap 52. A slight tension in the elastomeric element will be translated through the lanyards 80, 82 which pass through the loops 64, 66 in the straps 54, 56 for guidance. Although only single loops 64, 66 have been shown, it will clearly be possible to provide several loops in each of the straps so that the device can be modified to take the lanyards to any one or more of the four fingers. Only the loops necessary to align the lanyards with the finger 32 have been included to simplify the drawing.

The lanyards pass through the openings 88 in the proximal attachment 70 where the lanyards are free to slide and then terminate at the distal attachment 68.

Figure 4:
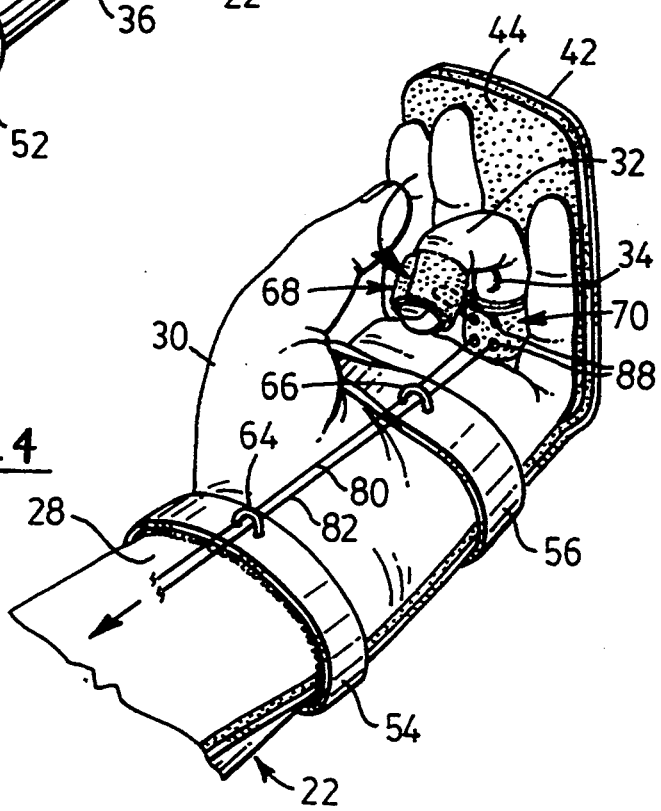
FIG. 4 is a view similar to 3 and showing a portion of the device to illustrate therapy of the hand using the device.

In use there are two conditions. Firstly, the exerciser can be used without the assistance of the elastomeric loop 92. If this loop is unstretched or simply not used, the user can grip the lanyards 80, 82 and then by pulling them along the user's arm away from the hand, the lanyards will transmit a load via the attachment 70 to the distal attachment 68 to fully bend the finger. The line of action on the attachment 68 is dictated by the direction of the lanyards leaving the proximal attachment 70. Since the respective attachments are substantially at the mid points of the proximal and distal bones and relatively close to the bones, the force on the proximal attachment will tend to be similar to that developed by the natural tendons in the finger which are normally actuated to bend the finger. These tendons work entirely in tension resulting in compressive loading in the finger and resulting bending of the finger due to the offset location of the tendons. This natural relationship of forces is closely mimicked by the arrangement of the lanyards and attachments 68, 70 on the finger. As a result, when the lanyards are pulled, the finger will be bent as shown in FIG. 4. This is achieved without applying tensile forces to the finger which is contrasted with prior art devices which simply apply a load to the distal tip of the finger to pull the finger down towards the hand. While this results in some bending of the finger, the amount of bending is limited and the forces applied tend to be tensile. As a result the bending may well cause pain which deters the patient from maintaining movement which is essential to limit adverse scar adhesions.

The elastomeric loop is attached in the position shown in FIG. 3 and some small preload tension is applied. This will tend to bend the finger without the user activating the finger, and then the user can work against this tension to straighten the finger using the tendons that have not been damaged, i.e. the tendons on the outer side of the finger. This is a desirable post-operative exercise to ensure the minimization of detrimental scar tissue about the tendons and muscles which would inhibit or even prevent movement should this scar tissue be allowed to heal completely. It is preferable that there be substantially continuous movement so that healing will take place without limiting these natural actions.

The amount of bending and tension can be increased either by shortening the elastomeric loop 92, or by shortening the lanyards 80, 82. Alternatively, a variety of elastomeric loops can be provided to give grades of loading to gradually strengthen the finger.

It should be noted that the basic essentials have been described of a preferred embodiment. Further refinements can be added. For instance, the distal attachment 68 could be provided with a second lanyard passing through suitable openings in the finger stop 42 to the outer side of the finger stop so that by pulling this lanyard, the finger will be straightened. Consequently it is possible to provide both the lanyards shown in FIG. 3 and the secondary lanyard so that the finger can be bent and straightened using the lanyards. This will result in predetermined directions of pull to limit the possibility of applying hurtful misaligned loads on the finger.

It should also be noted that the angle of the splint stop behind the fingers can be changed relative to the rest of the splint. This would be done as the wound hems to provide a greater range of movement for the exercise.

The arrangements of the straps can be varied, and the material and actual shape of the splint can be varied depending upon the requirements. Also, the number of finger attachments 68, 70 could be increased to 3 if it is necessary to attach one to each of the finger bones. All of this is within the scope of the invention which provides for controlled therapy of a damaged finger. These and other variations are within the scope of the invention as claimed.

I claim:

1. A device for use in therapy of the human hand, the device comprising:

a combination of a splint and an exerciser, the splint including a generally straight support shaped to receive at least the user's wrist and hand and a finger stop dependent from and angled with respect to said support to maintain the fingers in an angled position with respect to the palm of the hand, straps combining with said support for use to trap the user's wrist and hand in the splint with the fingers against the finger stop, and the exerciser including distal and proximal finger attachments adjustable for attachment to a damaged finger with the distal attachment positionable adjacent the finger tip and the proximal attachment positionable adjacent the root of the finger, at least one lanyard anchored to the distal attachment and slidably coupled to the proximal attachment so that the user can pull the lanyard whereby the lanyard slides through the proximal attachment and applies a force to the distal attachment to bend the finger in a substantially natural manner.

2. A device as claimed in claim 1 and further comprising a resilient member attached to the lanyard so that by attaching the resilient member to one of said straps a tensile force can be applied to bend the finger using energy stored in the resilient member whereby the user can exercise the finger by repetitively straightening the finger against the finger stop of the splint and allowing the resilient member to bend the finger.

3. A device as claimed in claim 2 in which at least one of the straps includes a loop to guide the lanyard.

4. A device as claimed in claim 2 in which there are two lanyards meeting at a bight in the distal attachment.

5. A device as claimed in claims 1 or 2 in which the splint is shaped from a thermoplastic material.

6. In a device for use in therapy of the human hand, the device having:
   a splint and an exerciser, the splint including a generally straight support shaped to receive at least the user's wrist and hand and a finger stop dependent from and angled with respect to said support to maintain the fingers in an angled position with respect to the palm of the hand, straps combining with said support for use to trap the user's wrist and hand in the splint with the fingers against the finger stop, and the exerciser including a lanyard to be anchored to the finger so that the user can pull the lanyard to exercise the finger, the improvement in which the exerciser includes distal and proximal finger attachments adjustable for attachment to a damaged finger with the distal attachment positionable adjacent the finger tip and the proximal attachment positionable adjacent the root of the finger, the lanyard being anchored at the distal attachment and slidably coupled to the proximal attachment whereby the lanyard slides through the proximal attachment and applies a force to the distal attachment to bend the finger in a substantially natural manner.

7. A device as claimed in claim 6 and further comprising a resilient member attached to the lanyard so that by attaching the resilient member to one of said straps a tensile force can be applied to bend the finger using energy stored in the resilient member whereby the user can exercise the finger by repetitively straightening the finger and allowing the resilient member to bend the finger.

* * * * *